United States Patent [19]

Zanno et al.

[11] Patent Number: 4,766,246

[45] Date of Patent: Aug. 23, 1988

[54] L-AMINODICARBOXYLIC ACID ESTERS

[75] Inventors: Paul R. Zanno, Nanuet; Ronald E. Barnett, Suffern; Glenn M. Roy, Garnerville, all of N.Y.

[73] Assignee: General Foods Corporation, White Plains, N.Y.

[21] Appl. No.: 898,063

[22] Filed: Aug. 19, 1986

[51] Int. Cl.$^4$ ............................................. C07C 69/74
[52] U.S. Cl. ................................... 560/117; 560/118; 560/119; 560/120; 560/121; 560/122; 560/123; 560/124; 560/125; 560/126; 560/127
[58] Field of Search ............... 560/117, 118, 119, 120, 560/121, 122, 123, 124, 125, 126, 127

[56] References Cited

FOREIGN PATENT DOCUMENTS

| 168112 | 1/1986 | European Pat. Off. | 117/ |
| 61-200999 | 3/1985 | Japan | 560/117 |
| 61-291596 | 6/1985 | Japan | 560/117 |
| 61-291597 | 6/1985 | Japan | 560/117 |

OTHER PUBLICATIONS

Chem. Abstr., vol. 93, (1980) 112439b.
Journal of Med. Chem. (1981) vol. 24, 573-583.
"An Exploration on the Molecular Recognition of Sweet Taste with an Induced Fit Model of Gustatory Receptor", Journal of Molecular Science, Dec., 1981, vol. 2 (published in the People's Republic of China).
"Structure Sweetness Relationship of L-Aspartic Acid Dipeptides, published by Shanghai Institute of Organic Chemistry", J. of Org. Chem. (Chinese), 16 (1982), People's Republic of China.
"Molecular Discrimination in the Sense of Taste", Zeng Guangzhi, Science Press, Beijing (Jul. 1984, People's Republic of China).

Primary Examiner—Delbert R. Phillips
Attorney, Agent, or Firm—Linn I. Grim; Daniel J. Donovan

[57] ABSTRACT

Sweeteners of the formula:

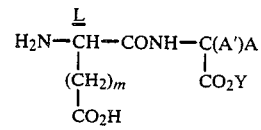

and food-acceptable salts thereof, where the substituents are disclosed herein.

2 Claims, No Drawings

L-AMINODICARBOXYLIC ACID ESTERS

This invention is a continuation-in-part of copending U.S. application Ser. No. 723,603 filed on Apr. 15, 1985, now abandoned.

This invention relates to a novel group of compounds and more particularly to a novel group of compounds particularly well suited as sweeteners in edible foodstuff.

Sweetness is one of the primary taste cravings of both animals and humans. Thus, the utilization of sweetening agents in foods in order to satisfy this secondary desire is well established.

Naturally occuring carbohydrate sweeteners such as sucrose, are still the most widely used sweetening agents. While thse naturally occurring carbohydrates, i.e., sugars, generally fulfill the requirements of sweet taste, the abundant usage thereof does not occur without deleterious consequence, e.g., high caloric intake and nutritional imbalance. In fact, oftentimes the level of these sweeteners required in foodstuffs is far greater than the level of the sweetener that is desired for economic, dietetic or other functional consideration.

In an attempt to eliminate the disadvantages concomitant with carbohydrate sweeteners, considerable research and expense have been devoted to the production of artificial sweeteners, such as for example, saccharin, cyclamate, dihydrochalcone, aspatame, etc. While some of these artificial sweeteners satisfy the requirements of sweet taste without caloric input, and have met with considerable commercial success, they are not, however, without their own inherent disadvantages. For example, many of these artificial sweeteners have the disadvantages of high cost, as well as delay in the perception of the sweet taste, persistent lingering of the sweet taste, and very objectionable bitter, metallic aftertaste when used in food products.

Since it is believed that many disadvantages of artificial sweeteners, particularly aftertaste, is a function of the concentration of the sweetener, it has been previously suggested that these effects could be reduced or eliminated by combining artificial sweeteners such as saccharin, with other ingredients such as aspartame or natural sugars, such as sorbitol, dextrose, maltose, etc. These combined products, however, have not been entirely satisfactory either. Some U.S. Patents which disclose sweetener mixtures include for example, U.S. Pat. No. 4,228,198; U.S. Pat. No. 4,158,068; U.S. Pat. No. 4,154,862; and U.S. Pat. No. 3,717,477.

Accordingly, much work has continued in an attempt to develop and identify compounds that have a sweet taste and which will satisfy the need for better lower calorie sweeteners, and so research continues for sweeteners that have intense sweetness, that is, deliver a sweet taste at low use levels and which will also produce enough sweetness at higher levels to act as sole sweetener for most sweetener applications. Furthermore, the sweeteners sought must have good temporal and sensory qualities. Sweeteners with good temporal qualities produce a time-intensity sweetness response similar to carbohydrate sweeteners without lingering. Sweeteners with good sensory qualities lack undesirable off tastes and aftertaste. Furthermore, these compounds must be economical and safe to use.

In U.S. Pat. No. 3,798,204, L-aspartyl-O-t-butyl-L-serine methyl ester and L-aspartyl-O-t-amyl-L-serine methyl ester are described as sweet compounds having significant sweetness.

In U.S. Pat. No. 4,448,716 metal complex salts of dipeptide sweeteners are disclosed. In the background of this patent a generic formula is described as an attempt to represent dipeptide sweeteners disclosed in five prior patents: U.S. Pat. No. 3,475,403; U.S. Pat. No. 3,492,131; Republic of South Africa Pat. No. 695,083 published July 10, 1969; Republic of South Africa Pat. No. 695,910 published Aug. 14, 1969; and German Pat. No. 2,054,554. The general formula attempting to represent these patents is as follows:

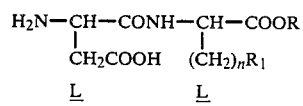

wherein R represents the lower alkyls, lower alkylaryls and cycloalkyls, n stands for integers 0 through 5, $R_1$ represents (a) phenyl group, (b) lower alkyls, (c) cycloalkyls, (d) $R_2$.

Where $R_2$ is hydroxy, lower alkoxy, lower alkyl, halogen, (e) $S(O)_m$ (lower alkyl) where m is 0, 1 or 2 and provided n is 1 or 2, (f) $R_3$.

Where $R_3$ represents hydroxy or alkoxy and (g) single or double unsaturated cycloalkyls with up to eight carbons. These compounds also are not entirely satisfactory in producing a high quality sweetness or in producing a sweet response at lower levels of sweetener.

Dipeptides of aspartyl-cysteine and aspartyl-methionine methyl esters are disclosed by Brussel, Peer and Van der Heijden in *Chemical Senses and Flavour*, 4, 141–152 (1979) and in *Z. Lebensm. Untersuch-Forsch.*, 159, 337–343 (1975). The authors disclose the following dipeptides:

α-L-Asp-L-Cys(Me)-OMe
α-L-Asp-L-Cys(Et)-OMe
α-L-Asp-L-Cys(Pr)-OMe
α-L-Asp-L-Cys(i-Pr)-OMe
α-L-Asp-L-Cys(t-But)-OMe
α-L-Asp-L-Met-OMe

In U.S. Pat. No. 4,399,163 to Brennan et al., sweeteners having the following formulas are disclosed:

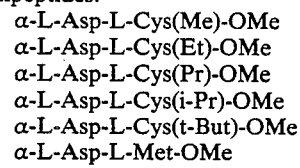

and physiologically acceptable cationic and acid addition salts thereof wherein
$R^a$ is $CH_2OH$ or $CH_2OCH_3$;
R is a branched member selected from the group consisting of fenchyl, diisopropylcarbinyl, d-methyl-t-butylcarbinyl, d-ethyl-t-butyl-carbinyl, 2-methylthio-2,4-dimethylpentan-3-yl, di-t-butyl-carbinyl,

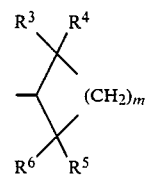

-continued

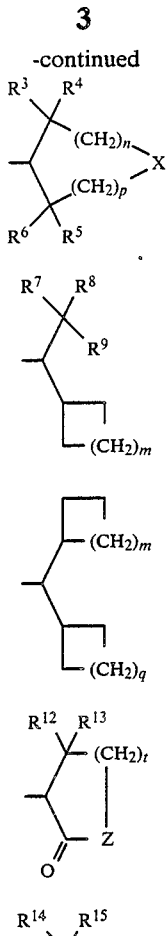

In a related patent, U.S. Pat. No. 4,411,925, Brennan, et al. disclose compounds of the above general formula with R being defined hereinabove, except $R^a$ is defined as methyl, ethyl, n-propyl or isopropyl.

U.S. Pat. No. 4,375,430 to Sklavounos discloses dipeptide sweeteners which are aromatic sulfonic acid salts of L-aspartyl-D-alaninamides or L-aspartyl-D-serinamides.

European Patent Application No. 95772 to Tsau describe aspartyl dipeptide sweeteners of the formula:

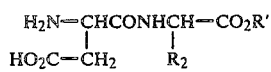

wherein R' is alkyl of 1 to 6 carbons, and $R_2$ is phenyl, phenylalkylenyl, or cyclohexylalkenyl, wherein the alkenyl group has 1 to 5 carbons. Closely related is U.S. Pat. No. 4,439,460 to Tsau, et al. which describes dipeptide sweeteners of the formula:

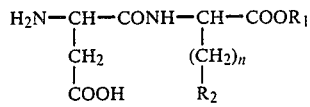

wherein n is an integer from 0 to 5, and $R_1$ is an alkyl, alkylaryl or alicyclic radical. Similar such compounds are described in many related patents, the major difference being the definition of $R_2$.

In U.S. Pat. No. 3,978,034 to Sheehan, et al., $R_2$ is defined as cycloalkenyl or phenyl. U.S. Pat. No. 3,695,898 to Hill defines $R_2$ as a mono- or a di-unsaturated alicyclic radical. Haas, et al. in U.S. Pat. No. 4,029,701 define $R_2$ as phenyl, lower alkyl or substituted or unsubstituted cycloalkyl, cycloalkenyl or cycloalkadienyl, or $S(O)_m$ lower alkyl provided that n is 1 or 2 and m is 0 or 2. Closely related are U.S. Pat. Nos. 4,448,716, 4,153,737, 4,031,258, 3,962,468, 3,714,139, 3,642,491, and 3,795,746.

U.S. Pat. No. 3,803,223 to Mazur, et al. describe dipeptide sweeteners and anti-inflammatory agents having the formula:

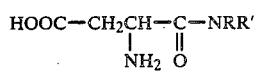

wherein R is hydrogen or a methyl radical and R' is a radical selected from the group consisting of alkyl, or

wherein Alk is a lower alkylene radical, X is hydrogen or hydroxyl, and Y is a radical selected from the group consisting of cyclohexyl, naphthyl, furyl, pyridyl, indolyl, phenyl and phenoxy.

Goldkamp, et al. in U.S. Pat. No. 4,011,260 describe sweeteners of the formula:

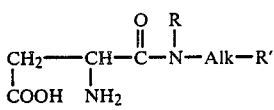

wherein R is hydrogen or a lower alkyl radical, Alk is a lower alkylene radical and R' is a carbocyclic radical. Closely related is U.S. Pat. No. 3,442,431.

U.S. Pat. No. 4,423,029 to Rizzi describes sweeteners of the formula:

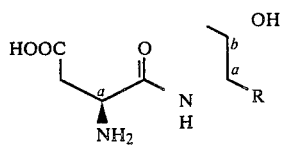

Wherein R is $C_4$-$C_9$ straight, branched or cyclic alkyl, and wherein carbons a, b and c have the (S) configuration.

European Patent Application No. 48,051 describes dipeptide sweeteners of the formula:

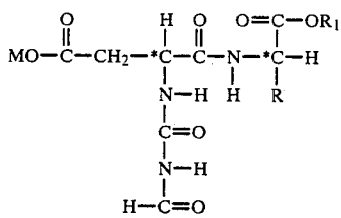

wherein
M represents hydrogen, ammonium, alkali or alkaline earth,
R represents

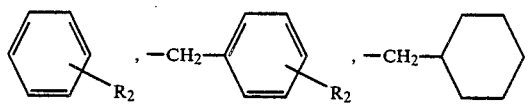

$R_1$ represents methyl, ethyl, propyl,
$R_2$ represents —OH, or $OCH_3$,
* signifies an L-optical configuration for this atom.

German Patent Application No. 7259426 discloses L-aspartyl-3-fenchylalanine methyl ester as a sweetening agent.

U.S. Pat. No. 3,971,822 to Chibata, et al., disclose sweeteners having the formula

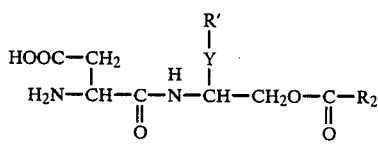

wherein R' is hydrogen or hydroxy, $R_2$ is alkyl of one to five carbon atoms, alkenyl of two to three carbon atoms, cycloalkyl of three to five carbon atoms or methyl cycloalkyl of four to six carbon atoms and Y is alkylene of one to four carbon atoms.

U.S. Pat. No. 3,907,366 to Fujino, et al. discloses L-aspartyl-aminomalonic acid alkyl fenchyl diester and its' physiologically acceptable salts as useful sweeteners. U.S. Pat. No. 3,959,245 disclose the 2-methyl cyclohexyl analog of the abovementioned patent.

U.S. Pat. No. 3,920,626 discloses N-α L-aspartyl derivatives of lower alkyl esters of O-lower-alkanoyl-L-serine, β-alanine, γ-aminobutyric acid and D-β-aminobutyric acid as sweeteners.

Miyoshi, et al. in *Bulletin of Chemical Society of Japan*, 51, p. 1433–1440 (1978) disclose compounds of the following formula as sweeteners:

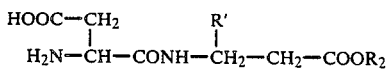

wherein R' is H, $CH_3$, $CO_2CH_3$, or benzyl and $R_2$ is lower alkyl or unsubstituted or substituted cycloalkyl.

European Patent Application No. 128,654 describes gem-diaminoalkane sweeteners of the formula:

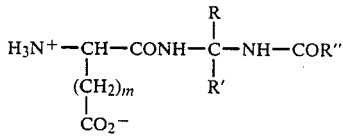

wherein m is 0 or 1, R is lower alkyl (substituted or unsubstituted), R' is H or lower alkyl, and R" is a branched alkyl, alkylcycloalkyl, cycloalkyl, polycycloalkyl, phenyl, or alkyl-substituted phenyl, and physiologically acceptable salts thereof.

U.S. Pat. No. 3,801,563 to Nakajima, et al. disclose sweeteners of the formula:

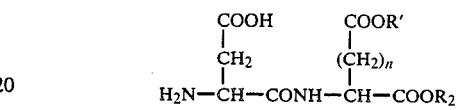

wherein R' is a branched or cyclic alkyl group of 3 to 8 carbon atoms, $R_2$ is a lower alkyl group of 1 to 2 carbon atoms and n is a integer of 0 or 1.

European Patent Application No. 34,876 describes amides of L-aspartyl-D-amino acid dipeptides of the formula:

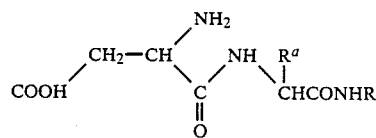

wherein $R^a$ is methyl, ethyl, n-propyl or isopropyl, and R is a branched aliphatic, alicyclic or heterocyclic member which is branched at the alpha carbon atom and also branched again at one or both of the beta carbon atoms. These compounds are indicated to be of significant sweetness.

In the *Journal of Medicinal Chemistry*, 1984, Vol. 27, No. 12, pp. 1663–8, are described various sweetener dipeptide esters, including L-aspartyl-α-aminocycloalkane methyl esters.

The various dipeptide esters of the prior art have been characterized as lacking significant stability at low pH values and/or thermal stability. These characteristics have limited the scope of use of these sweeteners in food products which are of low pH values or are prepared or served at elevated temperatures.

Accordingly, it is desired to find compounds that provide quality sweetness when added to foodstuffs or pharmaceuticals at low levels and thus eliminate or greatly diminish the aforesaid disadvantages associated with prior art sweeteners.

SUMMARY OF THE INVENTION

The present new compounds are esters of certain α-aminodicarboxylic acids and α-aminoesters which are low calorie sweeteners that possess a high order of sweetness with pleasing taste and higher stability at acid pH and elevated temperatures compared to known dipeptide sweeteners.

This invention provides new sweetening compounds represented by the formula:

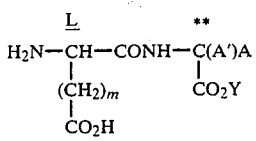

and food-acceptable salts thereof, wherein

A is hydrogen, alkyl containing 1-3 carbon atoms, hydroxyalkyl containing 1-3 carbon atoms or alkoxymethyl wherein the alkoxy contains 1-3 carbon atoms;

A' is hydrogen or alkyl containing 1-3 carbon atoms; alternatively;

A and A' taken together with the carbon atom to which they are attached form cycloalkyl containing 3-4 carbon atoms;

Y is $-(CHR_2)_n-R_1$ or $-CHR_3R_4$;

$R_1$ is an alkyl-substituted cycloalkyl, cycloalkenyl bicycloalkyl or bicycloalkenyl wherein at least one alkyl is in the $\beta$-position of the cycloalkyl, cycloalkenyl, bicycloalkyl or bicycloalkenyl ring, containing up to 7 ring carbon atoms and a total of 12 carbon atoms;

$R_2$ is H or alkyl containing 1-4 carbon atoms;

$R_3$ and $R_4$ are each cycloalkyl containing 3-4 ring carbon atoms;

n=0 or 1, and m=0 or 1, with the proviso that when the double asterisked carbon is an asymmetric or chiral center, the configuration around said carbon is in the D form.

DESCRIPTION OF THE PREFERRED EMBODIMENTS

In accordance with the present invention, the preferred compounds are those in which $R_1$ is an alkyl-substituted cycloalkyl or bicycloalkyl containing 5-7 ring carbon atoms and up to a total of 10 carbon atoms. Especially preferred are cycloalkyl substituted with at least one methyl group on the $\beta$ and/or $\beta'$ carbon atoms of the cycloalkyl ring. Particularly preferred cycloalkyls include cyclopropyl, cyclopentyl, and cyclohexyl and the preferred bicycloalkyl is fenchyl.

Also preferred are those compounds in which n=0. In those compounds in which n=1, $R_1$ is preferably a cyclopropyl group and $R_2$ is preferably tertiary butyl, isopropyl or cyclopropyl.

The groups representative of Y in the present new compounds include such groups as alkyl-substituted cycloalkyls, e.g., 1,2-dimethylcyclohexyl, 1,2-dimethylcyclopentyl, 1,2-dimethylcycloheptyl, 2,3-dimethylcyclopentyl, 2,3-dimethylcyclohexyl, 2,3-dimethylcycloheptyl, 2,4-dimethylcyclopentyl, 2,4-dimethylcyclohexyl, 2,4-dimethylcycloheptyl, 2,5-dimethylcyclopentyl, 2,5-dimethylcyclohexyl, 2,5-dimethylcycloheptyl, 2,6-dimethylcyclohexyl, 2,6-dimethylcycloheptyl, 2,7-dimethylcycloheptyl, 3,5-dimethylcyclopentyl, 4,5-dimethylcyclopentyl, 4,5-dimethylcycloheptyl, 3,6-dimethylcyclohexyl, 3,7-dimethylcycloheptyl, 4,6-dimethylcyclohexyl, 4,7-dimethylcycloheptyl, 5,6-dimethylcyclohexyl, 5,6-dimethylcycloheptyl, 5,7-dimethylcycloheptyl, 6,7-dimethylcycloheptyl, 2,2-dimethylcyclopentyl, 2,2-dimethylcyclohexyl, 2,2-dimethylcycloheptyl, 2,2,3-trimethylcyclopentyl, 2,2,3-trimethylcyclohexyl, 2,2,3-trimethylcycloheptyl, 2,2,4-trimethylcyclopentyl, 2,2,4-trimethylcyclohexyl, 2,2,4-trimethylcycloheptyl, 2,2,5-trimethylcyclopentyl, 2,2,5-trimethylcyclohexyl, 2,2,5-trimethylcycloheptyl, 2,3,3-trimethylcyclopentyl, 2,3,3-trimethylcyclohexyl, 2,3,3-trimethylcycloheptyl, 2,4,4-trimethylcyclopentyl, 2,4,4-trimethylcyclohexyl, 2,4,4-trimethylcycloheptyl, 1,2,3-trimethylcyclopentyl, 1,2,3-trimethylcyclohexyl, 1,2,3-trimethylcycloheptyl, 1,2,4-trimethylcyclopentyl, 1,2,4-trimethylcyclohexyl, 1,2,4-trimethylcycloheptyl, 1,2,5-trimethylcyclopentyl, 1,2,5-trimethylcyclohexyl, 1,2,5-trimethylcycloheptyl, 1,2,6-trimethylcyclohexyl, 1,2,6-trimethylcycloheptyl, 1,2,7-trimethylcycloheptyl, 2,3,4-trimethylcyclopentyl, 2,3,4-trimethylcyclohexyl, 2,3,4-trimethylcycloheptyl, 2,3,5-trimethylcyclopentyl, 2,3,5-trimethylcyclohexyl, 2,3,5-trimethylcycloheptyl, 2,3,6-trimethylcyclohexyl, 2,3,6-trimethylcycloheptyl, 2,3,7-trimethylcycloheptyl, 2,2,5,5-tetramethylcyclopentyl, 2,2,5,5-tetramethylcyclohexyl, 2,2,5,5-tetramethylcycloheptyl, 2,2,6,6-tetramethylcyclohexyl, 2,2,6,6-tetramethylcycloheptyl, 2,2,7,7-tetramethylcycloheptyl, 2,2,4,4-tetramethylcyclopentyl, 2,2,4,4-tetramethylcyclohexyl, 2,2,4,4-tetramethylcycloheptyl, 2,2,3,3-tetramethylcyclopentyl, 2,2,3,3-tetramethylcyclohexyl, 2,2,3,3-tetramethylcycloheptyl, 1,2,3,4-tetramethylcyclopentyl, 1,2,3,4-tetramethylcyclohexyl, 1,2,3,4-tetramethylcycloheptyl, 1,2,3,5-tetramethylcyclopentyl, 1,2,3,5-tetramethylcyclohexyl, 1,2,3,5-tetramethylcycloheptyl, 1,2,3,6-tetramethylcyclohexyl, 1,2,3,6-tetramethylcycloheptyl, 2,3,4,5-tetramethylcyclopentyl, 2,3,4,5-tetramethylcyclohexyl, 2,3,4,5-tetramethylcycloheptyl, 2,3,4,6-tetramethylcycloheptyl, 2,3,4,6-tetramethylcyclohexyl, 2,3,4,7-tetramethylcycloheptyl, 2,2,3,4-tetramethylcyclopentyl, 2,2,3,4-tetramethylcyclohexyl, 2,2,3,4-tetramethylcycloheptyl, 2,2,3,5-tetramethylcyclopentyl, 2,2,3,5-tetramethylcyclohexyl, 2,2,3,5-tetramethylcycloheptyl, 2,2,3,6-tetramethylcyclohexyl, 2,2,3,6-tetramethylcycloheptyl, 2,2,3,7-tetramethylcycloheptyl, 2,3,3,4-tetramethylcyclohexyl, 2,3,3,4-tetramethylcyclopentyl, 2,3,3,4-tetramethylcycloheptyl, 2,3,3,5-tetramethylcyclopentyl, 2,2,3,5-tetramethylcyclohexyl, 2,3,3,5-tetramethylcycloheptyl, 2,3,3,6-tetramethylcyclohexyl, 2,3,3,6-tetramethylcycloheptyl, 2,3,3,7-tetramethylcycloheptyl, 2,2,3,4-tetramethylcyclopentyl, 2,2,3,4-tetramethylcyclohexyl, 2,3,3,4-tetramethylcycloheptyl, 2,2,3,5-tetramethylcyclopentyl, 2,2,3,5-tetramethylcyclohexyl, 2,2,3,6-tetramethylcyclohexyl, 2,2,3,6-tetramethylcycloheptyl, 2,2,3,7-tetramethylcycloheptyl, 2,2,4,5-tetramethylcyclopentyl, 2,2,4,5-tetramethylcyclohexyl, 2,2,4,5-tetramethylcycloheptyl, 2,2,4,6-tetramethylcyclohexyl, 2,2,4,6-tetramethylcycloheptyl, 2,2,4,7-tetramethylcycloheptyl, dicyclopropylmethyl, t-butylcyclopropylmethyl, dicyclobutylmethyl, t-butylcyclobutylmethyl, etc.; -alkyl-substituted cycloalkenes, e.g., 2-methyl-3-cyclohexenyl, 2-methyl-3-cyclopentenyl, 2-methyl-3-cycloheptenyl, 2-methyl-4-cycloheptenyl, 5-methyl-3-cyclopentenyl, 2-methyl-2-cyclopentenyl, 2-methyl-2-cyclohexenyl, 2-methyl-2-cycloheptenyl, 2-methyl-2-cyclopentenyl, 6-methyl-2-cyclohexenyl, 7-methyl-2-cycloheptenyl, 2,3-dimethyl-2-cyclopentenyl, 2,3-dimethyl-2-cyclohexenyl, 2,4-dimethyl-2-cyclopentenyl, 2,4-dimethyl-2-cyclohexenyl, 2,5-dimethyl-2-cyclohexenyl, 2,5-dimethyl-2-cycloheptenyl, 2,6-dimethyl-2-cyclohexenyl, 2,6-dimethyl-3-cyclohexenyl, 2,5-dimethyl-3-cyclohexenyl, 2,5-dimethyl-2-cyclopentenyl, 2,4-dimethyl-3-cyclopentenyl, 2,4-dimethyl-3-cyclohexenyl, 4,5-dimethylcyclo-3-pentenyl, 5,5-dimethyl-3-cyclopentenyl, 6,6-dimethyl-3-cyclohexenyl, 1,2-dimethyl-3-cyclopentenyl, 1,2-dimethyl-3-cyclohexenyl, 1,5-dimethyl-3-cyclopentenyl, 2,2,6-trimethyl-3-cyclohexenyl, 2,2,5-trimethyl-3-cyclohexenyl, 2,5,5-trimethyl-3-cyclohexenyl, 2,7,7-trimethyl-3-cycloheptenyl, 2,7,7-trimethyl-4-cycloheptenyl, 2,2,7-trimethyl-3-cycloheptenyl, 2,2,7-trimethyl-4-cycloheptenyl, 2,3,6-trimethyl-3-cyclohexenyl, 2,3,7-trimethyl-3-cycloheptenyl, 2,3,5-trimethyl-3-cyclopentenyl, 2,2,6,6-tetramethyl-3-cyclohexenyl, 2,2,5,5-tetramethyl-3-cyclopentenyl, 2,2,7,7-tetramethyl-3-cycloheptenyl, 2,3,5,5-tetramethyl-3-cyclopentenyl, 2,3,6,6-tetramethyl-3-cyclohexenyl, 2,3,7,7-tetramethyl-3-cycloheptenyl, 2,3,6,6-tetramethyl-3-cycloheptenyl, 2,3,5,5-tetramethyl-3-cyclohexenyl, 2,3,4,5-tetramethyl-3-cyclopentenyl, 2,3,4,5-tetramethyl-3-cyclohexenyl, etc.; bicyclic compounds, such as norbornyl, norcaranyl, norpinanyl, bicyclo [2.2.2] octyl, etc.; alkyl substituted bicyclic compounds, e.g., 6,6-dimethyl-bicyclo [3.1.1] heptyl, 6,7,7-trimethylnorbornyl (bornyl or camphanyl), pinanyl, thujanyl, caranyl, fenchyl, 2-norbornylmethyl, etc.; unsubstituted and alkyl-substituted bicycloalkenes such as norbornenyl, norpinenyl, norcarenyl, 2-(4-norbornenyl)methyl, pinenyl, carenyl, fenchenyl, etc.; and tricyclo compounds such as adamantyl and alkyl-substituted adamantyl, etc.

The preferred $R_1$ is cycloalkyl or bicycloalkyl or alkyl-substituted cycloalkyl or bicycloalkyl, especially where the alkyl group is in the $\beta$ or $\beta'$ positions. Further, preference exists for compounds in which $R_1$ is a cycloalkyl with two, three or four alkyl groups in the $\beta$, $\beta'$ positions such as $\beta, \beta, \beta', \beta'$-tetraalkyl-substituted cyclopentyl, cyclobutyl, cyclohexyl, and cycloheptyl as well as $\beta, \beta, \beta'$-trialkyl substituted cyclobutyl, cyclopropyl, cyclohexyl, cyclopentyl, and cycloheptyl, and fenchyl. Also preferred are $\beta$-alkylcycloalkyls in which the alkyl group is isopropyl or tertiary butyl.

These novel compounds are effective sweetness agents when used alone or in combination with other sweeteners in an ingesta, e.g., foodstuffs or pharmaceuticals. For example, other natural and/or artificial sweeteners which may be used with the novel compounds of the present invention include sucrose, fructose, corn syrup solids, dextrose, xylitol, sorbitol, mannitol, acetosulfam, thaumatin, invert sugar, saccharin, thiophene saccharin, meta-aminobenzoic acid, metahydroxybenzoic acid, cyclamate, chlorosucrose, dihydrochalcone, hydrogenated glucose syrups, aspartame (L-aspartyl-L-phenylalanine methyl ester) and other dipeptides, glycyrrhizin and stevioside and the like. These sweeteners when employed with the sweetness agents of the present invention, it is believed, could produce synergistic sweetness responses.

Furthermore, when the sweetness agents of the present invention are added to ingesta, the sweetness agents may be added alone or with nontoxic carriers such as the abovementioned sweeteners or other food ingredients such as acidulants, natural and artificial gums, bulking agents such as polycarbohydrates, dextrins, and other food approved carbohydrates and derivatives. Typical foodstuffs, and pharmaceutical preparations, in which the sweetness agents of the present invention may be used are, for example, beverages including soft drinks, carbonated beverages, ready to mix beverages and the like, infused foods (e.g. vegetables or fruits), sauces, condiments, salad dressings, juices, syrups, desserts, including puddings, gelatin and frozen desserts, like ice creams, sherbets, icings and flavored frozen desserts on sticks, confections, chewing gum, cereals, baked goods, intermediate moisture foods (e.g. dog food), toothpaste, mouthwash and the like.

In order to achieve the effects of the present invention, the compounds described herein are generally added to the food product at a level which is effective to perceive sweetness in the food stuff and suitably is in an amount in the range of from about 0.0005 to 2% by weight based on the consumed product. Greater amounts are operable but not practical. Preferred amounts are in the range of from about 0.001 to about 1% of the foodstuff. Generally, the sweetening effect provided by the present compounds are experienced over a wide pH range, e.g. 2 to 10 preferably 3 to 7 and in buffered and unbuffered formulations.

It is desired that when the sweetness agents of this invention are employed alone or in combination with another sweetner, the sweetener or combination of sweeteners provide a sucrose equivalent in the range of from about 2 weight percent to about 40 weight percent and more preferably from about 3 weight percent to about 15 weight percent in the foodstuff or pharmaceutical.

A taste procedure for determination of sweetness merely involves the determination of sucrose equivalency. Sucrose equivalence for sweeteners are readily determined. The amount of a sweetener that is equivalent to a given weight percent sucrose can be determined by having a panel of tasters taste solutions of a sweetener at known concentrations and match its sweetness to standard solutions of sucrose.

In order to prepare compounds of the present invention, several reaction schemes may be employed. In one reaction scheme, compounds of general formula II (protected α-aminodicarboxylic acid) and III (amino-ester compound) are condensed to form compounds of general formula IV. Subsequent removal of protecting groups B and Z from compounds of general formula IV give the desired compounds of general formula I:

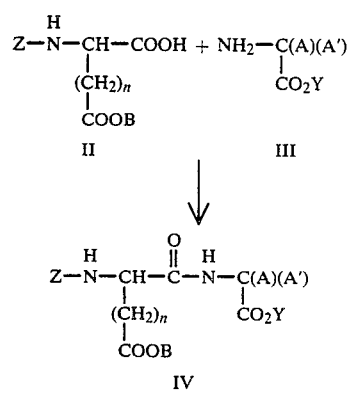

In these, group Z is an amino protecting group, B is a carboxyl protecting group, and A, A', Y, and n have the same meaning as previously described. A variety of protecting groups known in the art may be employed. Examples of many of these possible groups may be found in "Protective Groups in Organic Synthesis" by T. W. Green, John Wiley and Sons, 1981. Among the preferred groups that may be employed are benzyloxycarbonyl for A and benzyl for B.

Coupling of compounds with general formula III to compounds having general formula IV employs established techniques in peptide chemistry. One such technique uses dicyclohexylcarbodiimide (DCC) as the coupling agent. The DCC method may be employed with or without additives such as 4-dimethylaminopyridine or copper (II). The DCC coupling reaction generally proceeds at room temperature, however, it may be carried out from about −20° to 50° C. in a variety of solvents inert to the reactants. Thus suitable solvents include, but are not limited to, N,N-dimethyl-formamide, methylene chloride, toluene and the like. Preferably the reaction is carried out under an inert atmosphere such as argon or nitrogen. Coupling usually is complete within 2 hours but may take as long as 24 hours depending on reactants.

Various other methods can be employed to prepare the desired compounds. The following illustrates such methods using aspartic acid as the amino dicarboxylic acid.

For example, U.S. Pat. Nos. 3,786,039; 3,833,553; 3,879,372 and 3,933,781 disclose the reaction of N-protected aspartic anhydrides with amino acids and amino acid derivatives to yield the desired products. These N-protected aspartic anhydrides can be reacted with compounds of formula III by methods disclosed in the above patents. As described in U.S. Pat. No. 3,786,039 compounds of formula III can be reacted directly in inert organic solvents with L-aspartic anhydride having its amino group protected by a formyl, carbobenzloxy, or p-methoxycarbobenzloxy group which is subsequently removed after coupling to give compounds of general formula I. The N-acyl-L-aspartic anhydrides are prepared by reacting the corresponding acids with acetic anhydride in amounts of 1.0–1.2 moles per mole of the N-acyl-L-aspartic acid at 0° to 60° C. in an inert solvent. The N-acyl-L-aspartic anhydrides are reacted with preferably 1 to 2 moles of compounds of formula III in an organic solvent capable of dissolving both and inert to the same. Suitable solvents are, but not limited to, ethyl acetate, methyl propionate, tetrahydrofuran, dioxane, ethyl ether, N,N-dimethylformamide and benzene. The reaction proceeds smoothly at 0° to 30° C. The N-acyl group is removed after coupling by catalytic hydrogenation with palladium on carbon or with HBr or HCl in a conventional manner. U.S. Pat. No. 3,879,372 discloses that this coupling method can also be performed in an aqueous solvent at a temperature of −10° to 50° C. and at a pH of 4–12.

Another method for the synthesis of the desired compounds is the reaction of compounds of formula III with suitable aspartic acid derivatives in which protecting groups have been attached to the amino and beta-carboxy groups and the alpha carboxy group has been converted to a reactive ester function. As disclosed in U.S. Pat. No. 3,475,403 these coupled products may be deprotected as described to yield the desired compounds of formula I.

An alternative scheme to the desired coupled compounds involves reaction of compounds of formula III with L-aspartic acid N-thiocarboxyanhydride by the method of Vinick and Jung, Tet. Lett., 23, 1315–18 (1982). An additional coupling method is described by T. Miyazawa, Tet. Lett., 25, 771 (1984).

Compounds of general formula III are synthesized using art recognized techniques. For example, compounds of formula III can be synthesized by standard esterification methods known in the art by reacting the free acid or acid functional equivalents, such as esters or anhydrides, with the corresponding alcohols under ester-forming conditions, as for example in the presence of mineral acids, such as hydrochloric or sulfuric acids or organic acids, such as p-toluene-sulfonic acids. Reaction temperatures are in the range of −78° to reflux.

The reaction is carried out in a solvent that will dissolve both reactants and is inert to both as well. Solvents include, but are not limited to methylene chloride, diethyl ether, tetrahydrofuran, dimethylsulfoxide, N,N-dimethylformamide, and the like.

With regard to the removal of protecting groups from compounds of formula IV and N-protected precursors of formula III, a number of deprotecting techniques are known in the art and can be utilized to advantage depending on the nature of the protecting groups. Among such techniques is catalytic hydrogenation utilizing palladium on carbon or transfer hydrogenation with 1,4-cyclohexadiene. Generally the reaction is carried at room temperature but may be conducted from 5° to 65° C. Usually the reaction is carried out in the presence of a suitable solvent which may include, but are not limited to water, methanol, ethanol, dioxane, tetrahydrofuran, acetic acid, t-butyl alcohol, isopropanol or mixtures thereof. The reaction is usually run at a positive hydrogen pressure of 50 psi but can be conducted over the range of 20 to 250 psi. Reactions are generally quantitative taking 1 to 24 hours for completion.

In any of the previous synthetic methods the desired products are preferably recovered from reaction mixtures by crystallization. Alternatively, normal or reverse-phase chromatography may be utilized as well as liquid/liquid extraction or other means.

The desired compounds of formula I are usually obtained in the free acid form; they may also be recovered as their physiologically acceptable salts, i.e., the corresponding amino salts such as hydrochloride, sulfate, hydrosulfate, nitrate, hydrobromide, hydroiodide, phosphate or hydrophosphate; or the alkali metal salts such as the sodium, potassium, lithium, or the alkaline earth metal salts such as calcium or magnesium, as well as aluminum, zinc and like salts.

Conversion of the free peptide derivatives of formula I into their physiologically acceptable salts is carried out by conventional means, as for example, bringing the compounds of formula I into contact with a mineral acid, an alkali metal hydroxide, an alkali metal oxide or carbonate or an alkaline earth metal hydroxide, oxide, carbonate or other complexed form.

These physiologically acceptable salts can also be utilized as sweetness agents usually having increased solubility and stability over their free forms.

It is known to those skilled in the art that the compounds of the present invention having asymmetric carbon atoms may exist in racemic or optically active forms. All of these forms are contemplated within the scope of the invention.

The compounds of the present invention have one asymmetric site, which is designated by an asterisk (*) in the formula below, and one pseudoasymmetric site which is designated by a double asterisk (**).

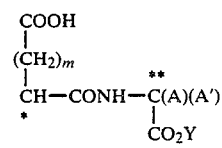

Furthermore, depending upon the substituent, Y may also contain chiral centers. All of the stereochemical configurations are encompassed within the above formula. However, the present invention is directed to compounds of the formula:

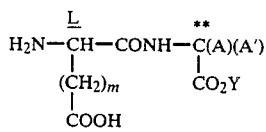

Although both D and L forms are possible, the present invention is directed to those compounds in which the dicarboxylic acid group is in the L-configuration as depicted in Formula I.

Whenever A is identical to A', or A and A' together form an unsubstituted cyclopropyl or cyclobutyl group, the compounds of the present invention have at least one asymmetric site, designated by the asterisk in the dicarboxylic acid moiety.

Whenever the group A and A' are different, the carbon atom designated by the double asterisk become as asymmetric center and a chiral center and the compounds of Formula I will contain at least two asymmetric centers. Furthermore, when A and A' taken together form a cyclopropyl or cyclobutyl ring having substituents, said carbon atom designated by the double asterisk may have an asymmetric center. In those cases wherein the carbon atom designated by the double asterisk is a chiral center, Formula I encompasses compounds of Formula II having the L, L configuration and Formula III having the L, D configuration:

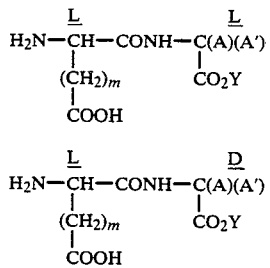

In the instance wherein the carbon designated by the double asterisk is a chiral center, the preferred compounds are those in which the configuration around the double asterisked carbon is in the D configuration. In the production of compounds of Formula I, the L, L diastereomer though not sweet itself, may be admixed with the L, D stereoisomers. The admixture of the L, L and L, D stereoisomers exhibit sweetness, but said mixture is not as sweet as the compound of Formula III (i.e., the L, D stereoisomer) in its pure form.

The following examples further illustrate the invention. In the following examples, the sensory evaluation were obtained by a panel of experts using known weight percent aqueous solutions of the exemplified compounds and were matched to sucrose standard solutions.

EXAMPLE 1

L-Aspartyl-D-alanine(2,2,5,5-tetramethyl-1-cyclopentyl)ester

To a magnetically stirred solution of 10 g (0.071 mol) 2,2,5,5-tetramethylcyclopentanone in 75 ml of dry tetrahydrofuran at 0° C. under argon is added 2.69 g (0.071 mol) of lithium aluminum hydride. When the reduction was complete, ethyl acetate was introduced dropwise to destroy unreacted lithium aluminum hydride. 25 mls of water is then added, followed by 300 mls of diethyl ether. The organic phase is washed with 100 mls of water, and dried over $MgSO_4$. Filtration followed by evaporation afforded 8.23 g of 2,2,5,5-tetramethylcyclopentanol.

To a stirred solution of 9.59 g (0.043 mol) N-Cbz-alanine in 50 ml dry $CH_2Cl_2$ containing 8.96 g (1 eq.) dicyclohexylcarbodiimide and 0.4 g dimethylaminopyridine (DMAP), all at 0° C., is added, via an addition funnel, 6.0 g (0.043 mol) of 2,2,5,5-tetramethylcyclopentanol dissolved in 50 ml $CH_2Cl_2$. After stirring for 48 hours, the mixture is filtered, and the filtrate is washed with 5% HCl (1×50 ml), saturated $NaHCO_3$ (1×50 ml), and water (1×50 ml). The organic layer is separated, dried over $MgSO_4$ and evaporated to yield 5.68 g of crude material, which after silica gel chromatography yielded 5.68 g of 2,2,5,5-tetramethylcyclopentyl N-Cbz-D-alanine ester.

5.68 g of 2,2,5,5-Tetramethylcyclopentyl N-Cbz-D-alanine ester is dissolved in 100 ml $CH_3OH$ and hydrogenated over 5% Pd/C in a Parr hydrogenation apparatus. When the reaction is complete the mixture is filtered through Celite and concentrated to yield 3.75 g of 2,2,5,5-tetramethylcyclopentyl alanine ester.

To a magnetically stirred solution of 3.75 g (0.017 mol) 2,2,5,5-tetramethylcyclopentyl alanine ester in 170 ml of dry dimethylformamide at 0° C. under atgon atmosphere is added 6.07 g (0.017 mol) N-Cbz-L-aspartic acid beta-benzyl ester followed by 2.28 g copper (II) chloride, and 3.54 g dicyclohexylcarbodiimide. This is stirred for 18 hours, after which the reaction mixture is poured into 200 ml 0.1N HCl and extracted with 300 ml ethyl acetate. The organic phase is washed with saturated $NaHCO_3$ and then water, and dried over $MgSO_4$. Evaporation of the solvent followed by silica gel chromatography yielded 5.14 g N-(N'-Cbz-L-aspartyl beta-benzyl ester)-D-alanine 2,2,5,5-tetramethyl-1-cyclopentyl ester.

2.0 g N-(N'-Cbz-L-aspartyl beta-benzyl ester)-D-alanine 2,2,5,5-tetramethyl-1-cyclopentyl ester is dissolved in 50 ml $CH_3OH$ and hydrogenated over 5% Pd/C in a Paar apparatus. Upon completion of the reaction th mixture is filtered and concentrated to yield 2.59 g L-aspartyl-D-alanine 2,2,5,5-tetramethyl-1-lcyclopentyl ester. $[\alpha]_D^{25}$ (pure) = +21.9°.

NMR (DMSO): δ0.8 (s, 6H), 1.00 (s, 6H), 1.3 (d, 3H), 1.45 (s, 4H), 2.2–2.4 (m, 2H), 4.35 (s, 1H), 4.75 (bris).

FAB-MS (m/z): 329 (M-H, 22%), 205 (20%), 90 (17%), 69 (100%).

Sweetness determination with this compound gave the following results:

| CONCENTRATION | SUCROSE EQUIVALENCE |
|---|---|
| 0.005 | 2.5 |
| 0.010 | 3.7 |
| 0.025 | 7.7 |
| 0.05 | 8.0 |

Similarly, by utilizing the appropriate alcohol, the following additional compounds are prepared:

N-L-Aspartyl-D-alanine(2,2,5-trimethylcyclopentyl)ester.

N-L-Aspartyl-D-alanine(2,5-dimethylcyclopentyl)ester.

N-L-Aspartyl-D-alanine(dicyclopropylmethyl)ester.

N-L-Aspartyl-D-alanine(fenchyl)ester.

N-L-Aspartyl-D-alanine(2-t-butylcyclopentyl)ester.

N-L-Aspartyl-D-alanine(1-t-butyl-1-cyclopropylmethyl)ester.

N-L-Aspartyl-D-alanine(1-isopropyl-1-cyclopropylmethyl)ester.

EXAMPLE 2

N-(L-Aspartyl)-2-methylalanine(2,2,5,5-tetramethyl-1-cyclopentyl)ester

To a stirred solution of 2 g (0.008 mol) of N-Cbz-2-aminoisobutyric acid in dry Cl(CH$_2$)$_2$Cl containing 1.9 g dicyclohexylcarbodiimide and 0.1 g dimethylaminopyridine (DMAP), all at 0° C., is added, via an addition funnel, 1.3 g of 2,2,5,5-tetramethylcyclopentanol dissolved in CH$_2$Cl$_2$. After stirring for 4 days, the mixture is filtered, and the filtrate is washed with 5% HCl (1×50 ml), saturated NaHCO$_3$ (1×50 ml), and water (1×50 ml). The organic layer is separated, dried over MgSO$_4$ and evaporated to yield N-Cbz-2-aminoisobutyric acid 2,2,5,5-tetramethylcyclopentyl ester.

N-Cbz-2-aminoisobutyric acid 2,2,5,5-tetramethylcyclopentyl ester is dissolved in CH$_3$OH and hydrogenated over 10% Pd/C in a Paar hydrogenation apparatus. When the reaction is complete the mixture is filtered through Celite and concentrated to yield 2-aminoisobutyric acid 2,2,5,5-tetramethylcyclopentyl ester (600 mg).

To a magnetically stirred solution of 0.6 g 2-aminoisobutyric acid 2,2,5,5-tetramethylcyclopentyl ester in 20 ml of dry dimethylformamide at 0° C. under argon atomsphere was added 1.02 g N-Cbz-L-aspartic acid beta-benzyl ester followed by 0.38 g of copper (II) chloride and 0.58 g dicyclohexylcarbodiimide. This is stirred for 18 hours, after which the reaction mixture is poured into 0.1N HCl and extracted with ethyl acetate. The organic phase is washed with saturated NaHCO$_3$ and then water, and dried over MgSO$_4$. Evaporation of the solvent yields N-(N'-Cbz-L-Aspartyl beta-benzyl ester)-2-methylalanine(2,2,5,5-tetramethyl-1-cyclopentyl)ester.

N-(N'-Cbz-L-Aspartyl beta-benzyl ester)-2-methylalanine(2,2,5,5-tetra-methyl-1-cyclopentyl)ester is dissolved in CH$_3$OH and hydrogenated over 5% Pd/C in a Parr apparatus. Upon completion of the reaction the mixture is filtered and concentrated to yield crude N-(L-Aspartyl)-2-methylalanine(2,2,5,5-tetramethyl-1-cyclopentyl)ester. Purification of the final product was done by reverse-phase chromatography on a Whatman Magnum 20 ODS-3 C$_{18}$ column; solvent system: 75% methanol in H$_2$O.

NMR (CDCl$_3$/DMSO): δ0.90 (s, 6H), 1.00 (s, 6H), 1.25–1.5 (m, 4H), 1.50 (s, 6H), 2.50–2.70 (q. of d., 2H), 3.50, 3.85 (br.s, 1H), 4.85 (br.s).

Sweetness determination with this compound gave the following results:

| CONCENTRATION | SUCROSE EQUIVALENCE |
|---|---|
| 0.005 | 2.00 |
| 0.010 | 3.25 |
| 0.025 | 5.75 |

Similarly, by utilizing the appropriate alcohol, the following additional compounds are prepared:

N-L-Aspartyl 2-methylalanine(2,2,5,-trimethylcyclopentyl)ester.

N-L-Aspartyl 2-methylalanine(2,5-dimethylcyclopentyl)ester.

N-L-Aspartyl 2-methylalanine(dicyclopropylmethyl)ester.

N-L-Aspartyl 2-methylalanine(fenchyl)ester.

N-L-Aspartyl 2-methylalanine(2-t-butylcyclopentyl)ester.

N-L-Aspartyl 2-methylalanine(1-t-butyl-1-cyclopropylmethyl)ester.

N-L-Aspartyl 2-methylalanine(1-isopropyl-1-cyclopropylmethyl)ester.

EXAMPLE 3

N-(L-Aspartyl)-1-amino-1-cyclopropanecarboxylic acid (2,2,5,5-tetramethyl-1-cyclopentyl)ester To a stirred solution of N-Cbz-1-aminocyclopropane carboxylic acid in dry (CH$_2$)$_2$Cl$_2$ containing dicyclohexylcarbodiimide and dimethylaminopyridine (DMAP), all at 0° C., is added, via an addition funnel, 2,2,5,5-tetramethylcyclopentanol dissolved in CH$_2$Cl$_2$. After stirring for 4 days, the mixture is filtered, and the filtrate is washed with 5% HCl (1×50 ml), saturated NaHCO$_3$ (1×50 ml), and water (1×50 ml). The organic layer is separated, dried over MgSO$_4$ and evaporated to yield N-Cbz-1-aminocyclopropanecarboxylic acid 2,2,5,5-tetramethylcyclopentyl ester.

N-Cbz-1-aminocyclopropanecarboxylic acid 2,2,5,5-tetramethylcyclopentyl ester is dissolved in absolute alcohol at 0° C. in an ultrasound bath. Palladium on carbon (10%) is added. The hydrogen source, 1,4-cyclohexadiene, is added, and ultrasound is commenced for eight minutes. The slurry is then filtered through a bed of Celite with ethyl alcohol. The solvent is removed by rotary evaporation to yield 1-aminocyclopropylcarboxylic acid 2,2,5,5-tetramethylcyclopentyl ester.

To a magnetically stirred solution of 1-aminocyclopropane carboxylic acid 2,2,5,5-tetramethylcyclopentyl ester is dry dimethylformamide at 0° C. under argon atmosphere is added N-Cbz-L-aspartic acid beta-benzyl ester followed by copper (II) chloride and dicyclohexylcarbodiimide. This is stirred for 18 hours, after which the reaction mixture is poured into 0.1N HCl and extracted with ethyl acetate. The organic phase is washed with saturated NaHCO$_3$ and then water, and dried over MgSO$_4$. Evaporation of the solvent yields N-(N'-Cbz-L-Aspartyl beta-benzyl ester)-1-amino-1-cyclopropanecarboxylic acid 2,2,5,5-tetramethyl-1-cyclopentyl ester.

The N-(N'-Cbz-L-Aspartyl-beta-benzyl ester)-1-amino-1-cyclopropanecarboxylic acid 2,2,5,5-tetramethyl-1-cyclopentyl ester is dissolved in absolute alcohol at 0° C. in an ultrasound bath. Palladium on carbon (10%) is added. The hydrogen source, 1,4-cyclohexadiene, is added, and ultrasound is commenced for eight minutes. The slurry is then filtered through a bed of Celite with ethyl alcohol. The solvent is removed by rotary evaporation to afford the final product.

Similarly, by utilizing the appropriate starting materials the following additional compounds are prepared:

N-L-aspartyl 1-aminocyclopropane-1-carboxylic acid(2,2,5,-trimethylcyclopentyl)ester.

N-L-aspartyl 1-aminocyclopropane-1-carboxylic acid(2,5-dimethylcyclopentyl)ester.

N-L-aspartyl 1-aminocyclopropane-1-carboxylic acid (dicyclopropylmethyl)ester.

N-L-aspartyl 1-aminocyclopropane-1-carboxylic acid (fenchyl)ester.

N-L-aspartyl 1-aminocyclopropane-1-carboxylic acid (2-t-butylcyclopentyl)ester.

N-L-aspartyl 1-aminocyclopropane-1-carboxylic acid (1-t-butyl-1-cyclopropylmethyl)ester.

N-L-aspartyl 1-aminocyclopropane-1-carboxylic acid (1-isopropyl-1-cyclopropylmethyl)ester.

The sweetness determination with L-Aspartyl-1-aminocyclopropyl-1-carboxylic acid, 2,5-dimethyl-1-cyclopentyl ester gave the following results:

| % Compound | Sucrose Equivalents | Sweetness relative to Sucrose (× Sucrose) |
|---|---|---|
| 0.005 | 1.0 | 200 |
| 0.010 | 2.2 | 217 |
| 0.025 | 3.3 | 133 |

EXAMPLE 4

N-L-Aspartyl-O-methyl-D-serine(2,2,5,-trimethylcyclopentyl)ester

To a solution of 5 g N-Cbz-D-serine 2,2,5-trimethylcyclopentyl ester in 50 ml dry $CH_2Cl_2$ is added 2 equivalents of $Ag_2O$ and 2 equivalents of methyl iodide. After stirring for 2 hours, the mixture is filtered and concentrated to yield the methyl ether of N-Cbz-D-serine 2,2,5-trimethylcyclopentyl ester. 3 g of N-Cbz-D-serine methyl ether 2,2,5-trimethylcyclopentyl ester is hydrogenated over 0.5 g 10% Pd/C in 100 ml $CH_3OH$. Upon completion, the mixture is filtered and concentrated to yield 3-methoxy-D-alanine 2,2,5-trimethylcyclopentyl ester. To a magnetically stirred solution of 2 g of 3-methoxy-D-alanine 2,2,5-trimethylcyclopentyl ester in 100 ml DMF at 0° C. is added 1 equivalent of N-Cbz-L-aspartic acid-β-benzyl ester followed by addition of 1 equivalent each of Cu(II) chloride and dicyclohexylcarbodiimide. After 18 hours the mixture is poured into 200 ml 0.1N HCl and extracted with 300 ml ethyl acetate. The organic phase is washed with saturated $NaHCO_3$, and $H_2O$, dried over $MgSO_4$, filtered and concentrated to an oil that is reconstituted in 50 ml $CH_3OH$ and hydrogenated over 0.5 g 5% Pd/C. Filtration followed by concentration yields L-aspartyl-D-serine 2,2,5-trimethylcyclopentyl ester methyl ether.

Using the appropriate starting materials, the following dipeptides are additionally prepared:

N-L-Aspartyl-O-methyl-D-serine(2,5-dimethylcyclopentyl)ester.

N-L-Aspartyl-O-methyl-D-serine(dicyclopropylmethyl)ester.

N-L-Aspartyl-O-methyl-D-serine(fenchyl)ester.

N-L-Aspartyl-O-methyl-D-serine(2-t-butylcyclopentyl)ester.

N-L-Aspartyl-O-methyl-D-serine(1-t-butyl-1-cyclopropylmethyl)ester.

N-L-Aspartyl-O-methyl-D-serine(1-isopropyl-1-cyclopropylmethyl)ester.

N-L-Aspartyl-O-methyl-D-serine(2,2,5,5-tetramethylcyclopentyl)ester.

EXAMPLE 5

L-Aspartyl-D-serine-(2,2,5-trimethylcyclopentyl)ester

Into a suspension of N-Cbz-D-serine (5 g) in 50 ml of dry THF containing 1 equivalent of 2,2,5-trimethylcyclopentanol is bubbled dry hydrogen chloride gas at room temperature. Upon complete solution of the mixture, the reaction is refluxed for 5 hours, then concentrated. Ethyl acetate is added, and this is washed with saturated sodium bicarbonate, water, and dried over $MgSO_4$. Filtration followed by concentration yields N-Cbz-D-serine-2,2,5-trimethylcyclopentyl ester. 5 g of this product is dissolved in 10 ml methanol and hydrogenated in a Paar apparatus over 1 g of 5% Pd/C to yield 2,2,5-trimethylcyclopentyl-D-serinate.

To a magnetically stirred solution of 0.1 mole 2,2,5-trimethylcyclopentyl-D-serinate in 100 ml dry DMF at 0° C. under an argon atmosphere is added 1 equivalent of N-Cbz-L-aspartic acid β-benzyl ester followed by addition of 1 equivalent each of Cu(II) chloride and dicyclohexylcarbodiimide. After 18 hours the mixture is poured into 200 ml 0.1N HCl and extracted with 300 ml ethyl acetate which is successively washed with saturated $NaHCO_3$, $H_2O$, and dried over $MgSO_4$. Filtration and evaporation yields N-Cbz-β-benzyl-L-aspartyl-D-serine 2,2,5-trimethylcyclopentyl ester. 2 g N-Cbz-β-benzyl-L-aspartyl-D-serine 2,2,5-trimethylcyclopentyl ester in 50 ml dry $CH_3OH$ is hydrogenated in a Paar apparatus over 5% Pd/C. Upon completion of the reaction, the mixture is filtered through Celite and concentrated to dryness to yield the final product.

Similarly, utilizing the appropriate starting materials the following additional compounds are prepared:

N-L-Aspartyl-D-serine(2,2,5-trimethylcyclopentyl)ester.

N-L-Aspartyl-D-serine(2,5-dimethylcyclopentyl)ester.

N-L-Aspartyl-D-serine(dicyclopropylmethyl)ester.

N-L-Aspartyl-D-serine(fenchyl)ester.

N-L-Aspartyl-D-serine(2-t-butylcyclopentyl)ester.

N-L-Aspartyl-D-serine(1-t-butyl-1-cyclopropylmethyl)ester.

N-L-Aspartyl-D-serine(1-isopropyl-1-cyclopropylmethyl)ester.

N-L-Aspartyl-D-serine(2,2,5,5-tetramethylcyclopentyl)ester.

EXAMPLE 6

N-L-Aspartyl-D-alanine(1-methyl-1-cyclopentyl)ester

A.

N-carbobenzoxy-D-alanine(1-methyl-1-cyclopentyl)ester

To a magnetically stirred solution of 22.3 g (0.1 mol) N-Cbz-D-alanine in 50 mls of dry dichloromethane containing 0.5 mls of concentrated sulfuric acid at 0° C., was added dropwise a 10 g (0.1 mol) sample of 1-methylcyclopentene in 50 mls of dichloromethane. After 5 days of stirring at room temperature, the mixture was heated to reflux for 4 hours, after which the reaction was cooled to room temperature, washed with 100 mls of saturated $NaHCO_3$, 100 mls of water and dried over $MgSO_4$. Filtration followed by evaporation of the solvent yielded 1.81 g of the product. NMR($CDCl_3$): δ1.3–1.4(d, 3H), 1.5(s, 3H), 1.5–1.7 (m, 8H), 4.2 (m, 1H), 5.05 (s, 2H), 5.25 (m, 1H), 7.3 (s, 5H).

B. D-Alanine(1-methylcyclopentyl)ester 1.8 g of the compound of part A was hydrogenated in 50 mls of methanol containing 0.5 g of 5% Pd/C catalyst in a Paar apparatus. The catalyst was filtered off, the solvent was removed by evaporation and 0.54 g of 1-methylcyclopentyl D-alanine ester was obtained.

C.
Beta-benzyl-N-carbobenzoxy-L-aspartyl-D-alanine-(1-methyl-1-cyclopentyl)ester To 0.54 g (0.0031 mol) of the product from B in 31 mls of dimethylformamide at 0° C. under an argon atmosphere is added 1.11 g (0.0031 mol) of N-Cbz-L-aspartic acid, betabenzyl ester, followed by 417 mg (1 equiv.) Cu (II) Cl$_2$ and 646 mg. (1 equiv.) dicyclohexylcarbodiimide. This is stirred for 16 hours, after which it is poured into 200 mls of 0.1N HCl and extracted with 3×100 ml of ethyl acetate. The organic phase was washed with 100 ml of water and dried over MgSO$_4$. Filtration and evaporation of the solvent yielded 1.0 g of beta-benzyl-N-carbobenzoxy L-aspartyl-D-alanine-(1-methyl-1-cyclopentyl)ester.

NMR (CDCl$_3$): δ1.3–1.4(d, 3H), 1.5 (s, 3H), 1.5–1.7 (m, 8H), 2.7–3.0 (d of d, 2H), 4.35 (m, 2H), 5.1 (s, 2H), 5.8 (d, 1H), 6.9 (d, 1H), 7.3 (s, 5H).

D.
N-L-aspartyl-D-alanine(1-methyl-1-cyclopentyl)ester 2.3 g of the product from C was hydrogenated over 0.5 g of Pd/C (5%) in methanol to yield 280 mg. L-aspartyl-D-alanine(1-methyl-1-cyclopentyl)ester.

NMR (D$_2$O): δ1.3–1.4(d, 3H), 1.5 (s, 3H), 1.5–1.7 (m, 8H), 2.3 (m, 2H), 4.2 (m, 2H).

Sweetness determination with this compound gave the following results:

| Percent of Compound | Sucrose Equivalence | Sweetness Value Relative to Sucrose (× Sucrose) |
|---|---|---|
| 0.05 | 2.0 | 40 |

EXAMPLE 7
N-L-Aspartyl-D-alanine(2,5-dimethylcyclopentyl)ester

A.
N-carbobenzoxy-D-alanine(2,5-dimethylcyclopentyl)ester

To a magnetically stirred solution of 19.63 g (0.008 mol) N-Cbz-D-alanine, 18.34 g (1 equiv.) of dicyclohexylcarbodiimide, and 0.88 g of 4-(dimethylamino)pyridine in 150 mls of dichloromethane at 0° C., is added 10 g (0.088 mol) of 2,5-dimethylcyclopentanol. After 48 hours, the reaction mixture is filtered to remove dicyclohexylurea and concentrated to a pale yellow oil, which is redissolved in ethyl acetate. This is successively washed with 100 mls of 5% HCl, 100 mls of saturated NaHCO$_3$, 100 mls of saturated NaCl and 100 mls of water, dried over MgSO$_4$ and filtered. Evaporation of the solvent afforded 23.7 of N-Cbz-D-alanine, 2,5-dimethylcyclopentylester.

B. D-Alanine-(2,5-dimethylcyclopentyl)ester 5.08 g of the product from A was hydrogenated several times over 0.5 g of 5% Pd/C in 50 mls of CH$_3$OH to yield 2.59 g of D-alanine-(2,5-dimethylcyclopentyl)ester.

C.
N-Cbz-beta-benzyl-L-aspartyl-D-alanine(2,5-dimethylcyclopentyl)ester

To a solution of 9.45 g (0.05 mol) of the product from B in 300 mls of dry DMF at 0° C. is added 17.85 g (1 eq.) of N-Cbz-beta-benzyl-L-aspartic acid, 6.72 g (1 eq.) copper (II) chloride and 10.42 g (1 eq.) dicyclohexylcarbodiimide. This, at 0° C. under an argon atmosphere, is stirred for 18 hours. The mixture is filtered to remove the urea, and is poured onto 300 mls of 0.1N HCl. The blue solution is extracted with 3×200 ml of diethyl ether and 3×200 ml of ethyl acetate. The combined organic phases were washed with 100 mls of NaHCO$_3$ (saturated), 100 mls of saturated NaCl, and 100 mls of water, and dried over MgSO$_4$. Filtration and evaporation afforded 29.6 g of the crude above-identified product, which was purified by flash silica gel chromatography.

D.
N-L-Aspartyl-D-alanine(2,5-dimethylcyclopentyl)ester

The product from C was hydrogenated in the usual fashion in methanol over 5% Pd/C to yield the final product. $[\alpha]_D^{25} = 2.7°$.

Sweetness determination with this compound gave the following results:

| Concentration | Sucrose Equivalence | Sweetness relative to Sucrose (× Sucrose) |
|---|---|---|
| 0.005 | 1.16 | 233 |
| 0.01 | 2.3 | 230 |
| 0.025 | 4.82 | 193 |
| 0.050 | 7.50 | 150 |

EXAMPLE 8
N-L-Aspartyl-1-amiocyclopropane carboxylic acid (2,2,5,5-tetramethyl-1-cyclopentyl)ester

A.
N-t-butoxycarbonyl-1-aminocyclopropanecarboxylic acid (1)

To a solution of 1-aminocyclopropanecarboxylic acid (3.03 g) in saturated aqeuous sodium bicarbonate (150 ml) was added a solution of di-t-butyldicarbonate (9.82 g) in t-butanol (50 ml), and the resulting mixture was stirred overnight. Water was then added and the mixture was washed with ethyl acetate. The aqueous phase was separated, made acid to pH 1 with concentrated hydrochloric acid and extracted twice with ethyl acetate. The combined extracts were washed with saturated sodium chloride, dried over magnesium sulfate, and the solvent was evaporated to yield a white solid. (4.77 g, 86%). NMR (CDCl$_3$): δ1.05–1.35 (m, 2H, cyclopropyl), 1.41 (s, 9H, t-butyl), 1.41–1.70 (m, 2H, cyclopropyl), 5.20, (br. s, 1H, NH), 9.25 (br. s, 1H, CO$_2$H).

B. 2,5-Dimethylcyclopentyl N-t-butoxycarbonyl-1-aminocyclopropanecarboxylate (2)

To a solution of 2,5-dimethylcyclopentanol (0.55 g.), compound 1 (0.97 g), and 4-(dimethylamino)pyridine (0.06 g.) in methylene chloride (100 ml) was added dicyclohexylacarbodiimide (1.09 g.), and the resulting mixture was stirred overnight. The precipitated dicyclohexylurea was removed by filtration, and the filtrate was evaporated. Ethyl acetate was then added to the residue, and the mixture was filtered again. The filtrate was washed with 1M hydrochloric acid, saturated aqeuous sodium bicarbonate, and water, dried over magnesium sulfate, and the solvent was evaporated to a colorless oil (1.18 g. 83%). The product was purified by column chromotography on silica gel, 4:1 hexane:ethyl acetate, eluent.

NMR (CDCl$_3$): δ0.92 (t, 6H, 2CH$_3$), 1.05–2.10 (m, 10H, cyclopentyl, cyclopropyl), 1.40 (s, 9H, t-Bu), 4.60 (dd., 1H, CO$_2$CH), 5.05 (br. s, 1H, NH).

C.
β-Benzyl-N-benzyloxycarbonyl-L-aspartyl-1-aminocyclopropanecarboxylic acid, 2,5-dimethylcyclopentyl ester (3)

A mixture of compound 2 (0.57 g), 95% ethanol (11 ml), water (7.5 mls) and concentrated hydrochloric acid (4 ml) was heated to reflux for 2 hours. The mixture was cooled, and 1 molar hydrochloric acid was added. The solution was washed with ethyl acetate. The separated aqueous phase was made basic with 1M sodium hydroxide and extracted twice with ethyl acetate. The combined extracts were washed with saturated sodium chloride, dried over magnesium sulfate, and the solvent was evaporated to yield 0.22 g of a colorless oil. Dicyclohexylcarbodiimide (0.25 g) was added to a solution of the above oil, followed by N-benzyloxycarbonyl-L-aspartic acid, beta-benzyl ester (0.40 g) and copper (II) chloride (0.17 g) in dimethyl formamide (10 mls). The resulting mixture was stirred overnight. The green mixture was then filtered to remove dicyclohexylurea, and 1M hydrochloric acid was added to the filtrate. This was extracted twice with ethyl acetate, and the combined extracts were washed with 1M hydrochloric acid, saturated sodium bicarbonate and saturated sodium chloride. The solution was dried over magnesium sulfate, and the solvent was evaporated to give 0.53 g of a yellow oil. This is purified by column chromatography on silica gel, 4:1 hexane:ethyl acetate, eluent, to give the desired product as a white solid (0.33 g, 32%). NMR (CDCl$_3$): δ0.91 (t, 6H, 2CH$_3$), 0.80–2.25 (m, 10H, cyclopropyl, cyclopentyl), 2.70 (dd., 1H, J$_1$=7 Hz, J$_2$=17 Hz, aspartyl CH$_2$), 3.00 (dd., 1H, J$_1$=5 Hz, J$_2$=17 Hz, aspartyl CH$_2$), 4.30–4.70 (m, 2H, CO$_2$CH, aspartyl CH), 5.10 (s, 4H, 2PhCH$_2$), 5.87 (br. d, 1H, NH), 6.95 (br. s, 1H, NH), 7.30 (s, 10H, 2Ph).

D. L-Aspartyl 1-aminocyclopropanecarboxylic acid, 2,5-dimethylcyclopentyl ester A mixture of compound 3 (0.31 g), 1,4-cyclohexadiene (0.46 g), 10% palladium-on-carbon (0.3 g) and 95% ethanol (10 ml) was placed in an ultrasonic bath for 10 minutes. The mixture was then filtered through Celite, and the solvent was evaporated to yield 130 mg of a colorless oil which solidified upon standing. This was purified by HPLC using a reverse phase C$_{18}$ column, 60% methanol in water as eluent to yield the desired product as a white solid (72 mg, 40%). MP: 155.5°–157° C. FAB MS (m/z): 313 (M+H, 22%) 217 (87%), 102 (69%), 88 (100%).

EXAMPLE 9
α-L-Aspartyl-2-methylalanine [β(+)Fenchyl]ester

N-CBZ-protected amino isobutyric acid (Chemical Dynamics, Inc.) was dissolved in 1,2-dichloroethane (50 mL) at 0° C. under argon. A solution of N,N-dimethylaminopyridine (0.5 equiv.) and β(+) fenchyl alcohol (1 equiv.) in 1,2-dichloroethane (10 mL) was added. Lastly, dicyclohexylcarbodiimide (1.1 equiv.) was added as a solid. After five days of stirring at room temperature the urea was removed by filtration and the filtrate was diluted with petroleum ether (50 mL). The solution was clarified again by filtration and the filtrate was hi-vacuum rotary evaporated to a paste. Column chromatography on silica gel with 15:1 petroleum ether/ethyl acetate gave the pure product in 75–79% yield as a white crystalline solid. NMR (CDCl$_3$): δ0.90 (s, 3H), 1.05 (s, 3H) 1.10 (s, 3H), 1.20–1.80 (m, 7H), 1.60 (s, 6H), 4.20 (s, 1H), 5.10 (s, 2H), 5.55 (s, 1H), 7.40 (s, 5H). [α]$_D^{25}$= −11.65° (MeOH) mp. 83°–85° C.

The ester from above was deprotected in the usual manner by hydrogenation with palladium on carbon (10%) in methanol to give a quantitative yield of the free-amino ester.

The amine was immediately dissolved in DMF and coupled to an aspartic acid precursor by the Copper (II) chloride procedure to give a 90% yield of N-CBZα-L-aspartic acid β-benzylesterα2-methylalanine[β(+)Fenchyl]ester. NMR (CDCl$_3$): δ0.90 (s, 3H), 1.05 (s, 3H), 1.10 (s, 3H), 1.20–1.80 (m, 7H), 1.6 (d, 6H) 2.70–3.15 (m, 2H), 4.1–4.2 (m, 1H), 4.20 (s, 1H), 4.60 (s, 1H), 5.10 (s, 4H), 5.60 (d, 1H), 5.90 (d, 1H), 5.90 (d, 1H), 7.40 (s, 10H). The product was deprotected by hydrogenation and purified by Rp C$_{18}$ column chromatography with 85:15 methanol:water eluant, [α]$_D^{25}$= −3.30° (MeOH) mp. 121°–3° C.

Sweetness determination with this compound gave the following results:

| Concentration | Sucrose Equivalence | Sweetness relative to Sucrose (× Sucrose) |
| --- | --- | --- |
| 0.00750 | 8.5% | 1133 |
| 0.00375 | 6.0% | 1600 |
| 0.00185 | 5.7% | 3100 |
| 0.00692 | 3.5% | 3800 |

EXAMPLE 10
α-L-Aspartyl-D-alanine [β(+) Fenchyl]ester

A. exo-β-(+)-Fenchol

To a refluxing suspension of 72.65 g aluminum isopropoxide in 300 ml of freshly distilled isopropyl alcohol, was added dropwise, 27.1 g R-(−)-fenchone in 50 ml isopropanol. The reaction was halted after six days when it was determined by gas chromatography (Carbowax 20M) that more than 50% of the ketone was reduced. It was also determined by capillary chromatography (Supelcowax 10) that the exo/endo ratio for the fenchol was 3/1. Upon cooling, the mixture was filtered and washed thoroughly with dichloromethane. The precipitate was dissolved in 5% HCl (100 ml) and extracted with dichloromethane (50 ml). The combined dichloromethane solutions were washed with 5% HCl (50 ml), saturated NaHCO$_3$ (50 ml) and water (50 ml) and dried over MgSO$_4$. Filtration and removal of the solvent afforded 23.44 g of an oil that was 40% unreacted fenchone and 60% α and β fenchol isomers.

A mixture of 12 g (0.78 mol) β and α-fenchols, 11.9 ml (1.1 eq) triethylamine and 15.9 g p-nitrobenzol chloride (1.1 g) in 500 mls dry dichlormethane was refluxed for 24 hours. The mixture ofβ/α esters was separated by silica gel flash chromatography using hexane:ethyl acetate (40:1). 6.0 g of the exo-fenchyl para-nitrobenzate was isolated, ([α]$_D^{25}$= −17.1° (in benzene). 3 g of fenchol (9/1; β/α) was obtained upon basic hydrolysis of the nitrobenzate ester (refluxing excess NaOH in methanol). β-(+)-fenchol; [α]$_D^{25}$= +23.4° (neat), NMR: δ0.95–1.8 (16H, m, CH$_2$, CH$_3$); 3.0 ppm (1H, s, CH—O).

B. N-Cbz-D-alanine, β-(+)-fenchyl ester

To a stirred solution of 1.3 g β-(+)-fenchol in 20 ml dry dichloromethane was added 1.9 g (0.0084 mol) N-Cbz D-alanine, and the solution was cooled to 0° C. Then, 0.113 g p-dimethylaminopyridine and 1.91 g dicyclohexylcarabodiimide were added. After 24 hours, the reaction was stopped and filtered. The solvent was evaporated and the oily residue was dissolved in diethyl ether, washed with 5% HCl (25 ml), saturated NaHCO$_3$ (25 ml), water (25 ml) and dried over MgSO$_4$. After filtration and solvent evaporation, the product was purified by silica gel chromatography to yield 1.86 g N-Cbz-D-alanine, β-(+)-fenchyl ester; $[\alpha]_D^{25} = +3.86°$.

NMR: δ0.8–1.8 ppm (19H, m, CH$_2$, CH$_3$); 4.2 ppm (1H, s, CH—O);

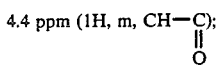

5.1 ppm (2H, s, CH$_2$—Ph) 5.4 ppm (1H, d, NH); 7.4 ppm (5H, s, Ph).

C. D-alanine, β(+)-fenchyl ester

The N-Cbz-D-alanine, β-(+)-fenchyl ester, (1.86 g) was dissolved in 50 ml methanol and hydrogenated over 0.1 g 5% Pd/C in a Paar shaker. After 2 hours the reaction was over; it was filtered through Celite, washed with methanol, concentrated and the crystallized residue was dissolved in dichloromethane.

D. N-Cbz-β-benzyl-L-aspartyl-D-alanine, β-(+)fenchyl ester

To the DMF solution containing the D-alanine ester (0.00355 mol) was added an equimolar amount of B-benzyl-N-Cbz-L-aspartic acid (1.27 g) and 0.526 g Cu(II)Cl$_2$. Upon solution of the CuCl$_2$, DCC (0.81 g) was added. After 24 hours, the reaction was complete, the urea was filtered and the solvent was evaporated. The yellow oil was dissolved in diethyl ether (25 ml) and washed with 5% HCl (25 ml), saturated NaHCO$_3$ (25 ml), and H$_2$O (25 ml). The ether layer was dried over MgSO$_4$ and evaporated to yield 0.95 g of product.

NMR: δ0.85–1.80 (19H, m, CH$_2$, CH$_3$), 4.2 ppm (1H, s, CH—O);

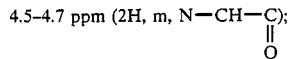

5.1 ppm (4H, s, OCH$_2$—Ph); 5.95 ppm (1H, d, NH); 7.05 ppm (1H, d, NH); 7.4 ppm (10H, s, Ph).

E. L-aspartyl-D-alanine, β-(+)-fenchyl ester 0.95 g protected dipeptide was dissolved in 50 ml methanol to which 0.1 g 10% Pd/C was added. This was hydrogenated in Paar shaker for 2 hours. The solution was filtered and evaporated to dryness to yield 0.194 g solid; $[\alpha]_D^{25} = -0.867°$.

The product was purified on reverse phase HPLC (85% methanol/water) to yield 75 mg L-aspartyl-D-alanine, β-(+)Fenchyl ester. NMR: δ0.8–1.8 (19H, m, CH$_2$, CH$_3$);

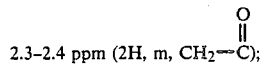

4.2 ppm (1H, s, OCH); 4.5 ppm (2H, m, N—CH);

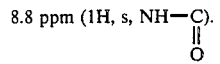

Sweetness determination with this compound gave the following results:

| Concentration | Sucrose Equivalence | Sweetness relative to Sucrose (× Sucrose) |
|---|---|---|
| 0.00750 | 9.0% | 1200 |
| 0.00375 | 8.6% | 2300 |
| 0.00185 | 6.5% | 3500 |
| 0.00092 | 4.7% | 5100 |

The compounds of this invention possess greater sweetness and higher stability in comparison to corresponding esters of the prior art.

What is claimed is:
1. N-L-Aspartyl-D-alanine [β(+)fenchyl]ester.
2. N-L-Aspartyl-2-methylalanine [β(+)Fenchyl]ester.

* * * * *

UNITED STATES PATENT AND TRADEMARK OFFICE
CERTIFICATE OF CORRECTION

PATENT NO. : 4,766,246

DATED : August 23, 1988

INVENTOR(S) : Paul R. Zanno et al.

It is certified that error appears in the above-identified patent and that said Letters Patent is hereby corrected as shown below:

On the front page, in the bibliographic data, after [22] Filed: Aug. 19, 1986, insert:

Related U.S. Application Data

[63] Continuation-in-part of Ser. No. 723,603 filed Apr. 15, 1985, now abandoned.

Signed and Sealed this

Twentieth Day of December, 1988

Attest:

DONALD J. QUIGG

*Attesting Officer*  *Commissioner of Patents and Trademarks*